(12) United States Patent
Vanacker

(10) Patent No.: US 7,122,036 B2
(45) Date of Patent: Oct. 17, 2006

(54) CONNECTOR FOR AN OSTEOSYNTHESIS SYSTEM INTENDED TO PROVIDE A CONNECTION BETWEEN TWO RODS OF A SPINAL OSTEOSYNTHESIS SYSTEM, OSTEOSYNTHESIS SYSTEM USING SUCH A CONNECTOR, AND METHOD OF IMPLANTING SUCH AN OSTEOSYNTHESIS SYSTEM

(75) Inventor: Gerard M. Vanacker, Saint Maur (FR)

(73) Assignee: Spinevision, S.A., (FR)

( * ) Notice: Subject to any disclaimer, the term of this patent is extended or adjusted under 35 U.S.C. 154(b) by 346 days.

(21) Appl. No.: 10/109,275

(22) Filed: Mar. 27, 2002

(65) Prior Publication Data

US 2002/0169448 A1    Nov. 14, 2002

Related U.S. Application Data

(63) Continuation-in-part of application No. 10/019,807, filed on Dec. 28, 2001, now abandoned.

(51) Int. Cl.
*A61B 17/56* (2006.01)
*A61B 17/58* (2006.01)
*A61F 2/30* (2006.01)

(52) U.S. Cl. ........................................................ 606/61

(58) Field of Classification Search ................. 606/60, 606/61, 72, 73
See application file for complete search history.

(56) References Cited

U.S. PATENT DOCUMENTS

| | | | | |
|---|---|---|---|---|
| 4,604,995 A | * | 8/1986 | Stephens et al. | 606/61 |
| 5,207,678 A | * | 5/1993 | Harms et al. | 606/61 |
| 5,429,637 A | * | 7/1995 | Hardy | 606/54 |
| 5,480,401 A | * | 1/1996 | Navas | 606/61 |
| 5,514,132 A | * | 5/1996 | Csernatony et al. | 606/61 |
| 5,534,002 A | * | 7/1996 | Brumfield et al. | 606/61 |
| 5,540,688 A | * | 7/1996 | Navas | 606/61 |
| 5,569,246 A | * | 10/1996 | Ojima et al. | 606/61 |
| 5,584,831 A | * | 12/1996 | McKay | 606/61 |
| 5,601,552 A | * | 2/1997 | Cotrel | 606/61 |
| 5,624,441 A | * | 4/1997 | Sherman et al. | 606/61 |
| 5,720,751 A | * | 2/1998 | Jackson | 606/86 |
| 5,755,796 A | * | 5/1998 | Ibo et al. | 623/17 |
| 5,776,135 A | * | 7/1998 | Errico et al. | 606/61 |
| 5,800,548 A | * | 9/1998 | Martin et al. | 606/61 |
| 5,947,967 A | * | 9/1999 | Barker | 606/61 |

(Continued)

FOREIGN PATENT DOCUMENTS

EP    0 446 092    9/1991

(Continued)

*Primary Examiner*—Eduardo C. Robert
*Assistant Examiner*—Anuradha Ramana
(74) *Attorney, Agent, or Firm*—Bachman & LaPointe

(57) ABSTRACT

A connector for an osteosynthesis system is intended to provide a connection between a rigid correction rod of circular cross section and a transverse connection element of a spinal osteosynthesis system. The connector comprises a hook having a first semicylindrical seat oriented substantially along a first axis to receive the correction rod in a sliding manner. The connector also having a second seat having an axis substantially perpendicular to the first axis. The second seat opening into the first seat to receive a substantially spherical end of a transverse rod of the transverse connection element. The second seat comprises a tapped hole with an axis oriented substantially perpendicular to the axis of the second seat in order to receive a clamping screw which will exert pressure on the spherical end of the transverse rod, the spherical end coming to bear on the correction rod.

9 Claims, 7 Drawing Sheets

U.S. PATENT DOCUMENTS

| | | | |
|---|---|---|---|
| 5,964,769 A * | 10/1999 | Wagner et al. | 606/74 |
| 6,099,528 A * | 8/2000 | Saurat | 606/61 |
| 6,187,005 B1 * | 2/2001 | Brace et al. | 606/61 |
| 6,290,196 B1 * | 9/2001 | Mayenberger | 248/274.1 |
| 6,468,276 B1 * | 10/2002 | McKay | 606/61 |
| 6,475,218 B1 * | 11/2002 | Gournay et al. | 606/61 |
| 6,554,831 B1 * | 4/2003 | Rivard et al. | 606/61 |
| 2002/0138077 A1 * | 9/2002 | Ferree | 606/61 |
| 2002/0143327 A1 * | 10/2002 | Shluzas | 606/61 |
| 2003/0045874 A1 * | 3/2003 | Thomas, Jr. | 606/61 |

FOREIGN PATENT DOCUMENTS

| | | |
|---|---|---|
| EP | 0 676 177 | 10/1995 |
| EP | 0 689 799 | 1/1996 |

* cited by examiner

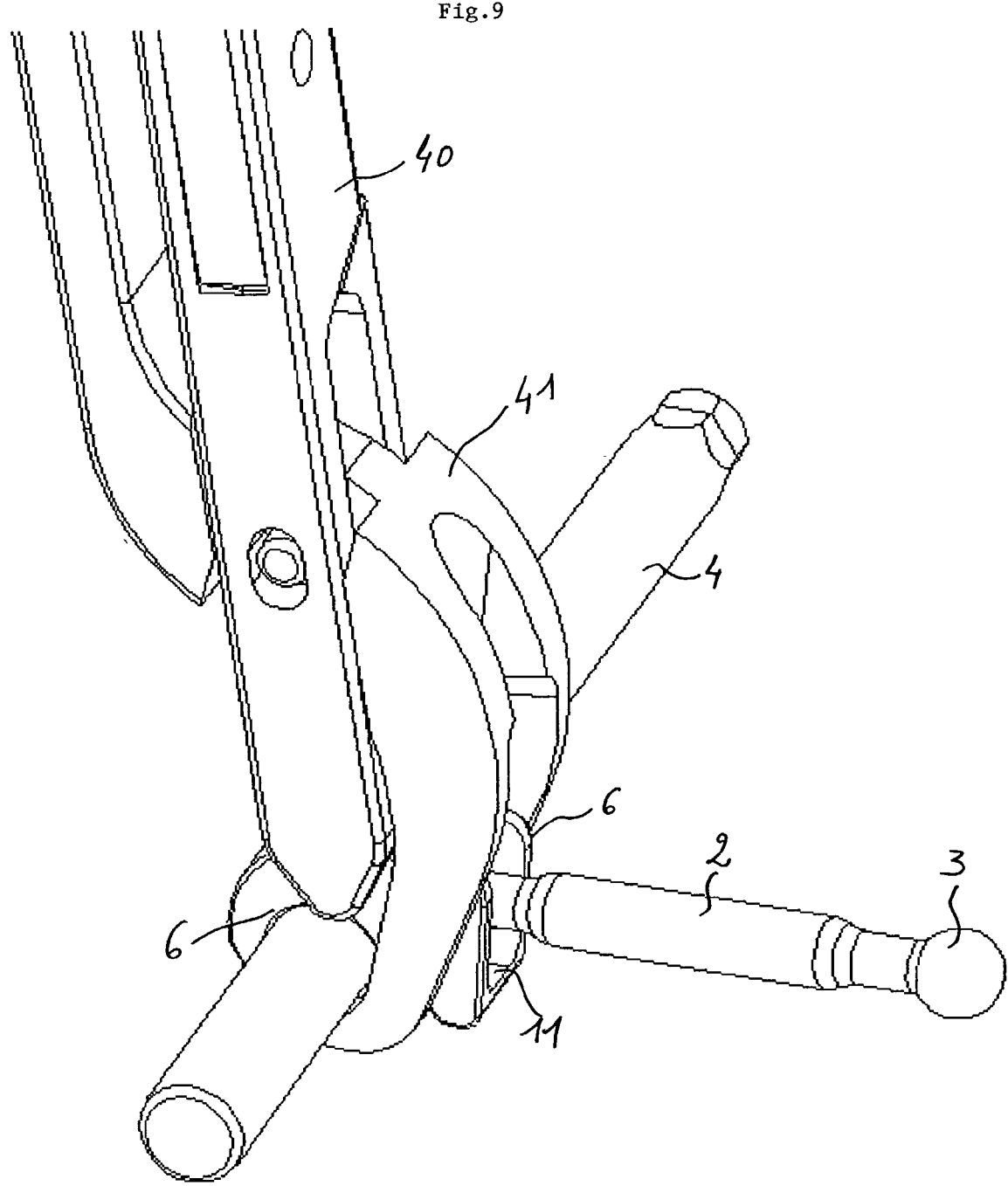

CONNECTOR FOR AN OSTEOSYNTHESIS SYSTEM INTENDED TO PROVIDE A CONNECTION BETWEEN TWO RODS OF A SPINAL OSTEOSYNTHESIS SYSTEM, OSTEOSYNTHESIS SYSTEM USING SUCH A CONNECTOR, AND METHOD OF IMPLANTING SUCH AN OSTEOSYNTHESIS SYSTEM

CROSS REFERENCE TO RELATED APPLICATION(S)

This application is a continuation-in-part of U.S. Ser. No. 10/019,807, filed Dec. 28, 2001, entitled TRANSVERSE CONNECTOR FOR SPINAL OSTEOSYNTHESIS SYSTEM, now abandoned.

BACKGROUND OF THE INVENTION

The present invention concerns the field of spinal osteosynthesis, and more particularly the field of correction of the alignment of the vertebrae by means of a system comprising correction rods, hooks which can be fixed on the vertebrae, and transverse connection rods.

Such systems form a torsionally rigid correction frame.

As an example of the prior art, reference may be made to European patent EP95910695, published under number EP750477. This patent describes in particular a fixation hook for interconnecting a correction rod of a spinal osteosynthesis system and a rigid transverse rod and for clamping the correction rod against the transverse rod, said fixation hook comprising:
  a body;
  a passage defined by edge portions in said body for receiving the transverse rod, said passage having a first height at least equal to the thickness of the transverse rod, extending along the entire length of said body, opening freely out at one end and terminating at one end in an aperture defined in said body, and having a second height exceeding the thickness of the transverse rod;
  a curved strip portion extending from said body so that a correction rod can lodge therein, said aperture being provided in a connection zone between said body and said curved strip portion;
  a tapped hole defined in said body, which hole opens into said passage and is positioned in such a way that the axis of said tapped hole is in proximity to a free end portion of said curved strip portion;
  a clamping screw inserted via a screwthread into said tapped hole in order to clamp a transverse rod in said passage on a correction rod lodged in said curved strip portion;
  by which means the clamping screw, when it clamps said transverse rod, exerts a clamping force along a line which is offset in proximity to the free end portion of said curved strip portion in relation to the central axis of the correction rod in such a way as to cause a pivoting movement of the transverse rod about said correction rod.

Another known European patent published under number EP446092 describes another device for rigid transverse connection between two spinal osteosynthesis rods. This device comprises two fixation elements, each consisting of a hook which is adapted to be able to engage on a rigid transverse rod in a sliding manner, and equipped with means for locking it on the transverse rod. This hook is made up of a body and two blades separated by a gap having a width corresponding to that of the transverse rod, and a support bearing for the hook on the transverse rod is formed on the body between the blades, which blades extend on each side of the transverse rod when the hook straddles the latter. Two hooks combined with a rectangular transverse rod form a relatively simple transverse connection device which can be fitted in place quickly and has a high degree of rigidity in torsion and in flexion.

The transverse connection systems of the prior art require perfect parallelism of the two connection elements formed by rods or plates. In the case where the rods are not parallel, the surgeon has to bend the transverse connection element to adapt the fixation elements on the connection elements.

The solutions in the prior art permit free fixation in the frontal plane or in the sagittal plane, or in a combination of these two planes of rotation. However, they do not permit all of the desired relative orientations. They do not make it possible to avoid the operation of adapting the transverse elements by torsion, or to avoid arrangements which are not favorable to the overall rigidity of the osteosynthesis system in relation to the prominence of the implants.

SUMMARY OF THE INVENTION

The object of the present invention is to remedy these shortcomings by making available a connector for an osteosynthesis system with which it is possible to obtain a correction system of great rigidity after clamping, but which permits a correction of the alignment of the transverse elements in the different planes, and guarantees a simultaneous locking of all the rods and correction elements. To this end, the invention concerns, in its most general sense, a connector for an osteosynthesis system intended to provide a connection between a rigid correction rod of circular cross section and a transverse connection element of a spinal osteosynthesis system, said connector comprising a hook having a first semicylindrical seat oriented substantially along a first axis to receive said correction rod in a sliding manner, in which the connector has a second seat having an axis substantially perpendicular to the first axis, said second seat opening into the first seat and being intended to receive a substantially spherical end of a transverse rod of the transverse connection element, said second seat comprising a tapped hole with an axis oriented substantially perpendicular to the axis of the second seat in receive a clamping screw which will exert a pressure on the spherical end of the transverse rod, said spherical end coming to bear on the correction rod.

An important advantage of such a connector is that of allowing the tensioning or compression of the frame by sliding the connectors along the rods after the frame has been fitted. Another advantage is that such a connector avoids the presence of protruding parts under the rod (anterior to the rod in relation to the patient), which makes it easier to fit in vivo.

The connector for an osteosynthesis system according to the invention is advantageously intended to provide a rigid connection between two correction rods and two hooks which are each positioned on one of the rods, by way of a transverse rod offering a certain degree of freedom prior to final fixation.

It is also advantageous for the second seat to open out via a widened conical portion in order to permit a cone of mobility of the transverse rod before the clamping screw is tightened.

It is also advantageous for the second seat to have a substantially semicylindrical shape along the axis of the tapped hole, in such a way as to connect the connector and the transverse rod while permitting a rotation of the transverse rod in relation to the connector at the spherical end inside of the second seat and in such a way as to retain the transverse rod in translation along its axis.

The opening of the semicylindrical seat preferably extends about 180°. Thus, its lower end is substantially at the same level as the lower quadrant of the correction rod and there is no constituent material of the connector in contact with the bone.

The invention also concerns an osteosynthesis system comprising at least one transverse connection element which has a transverse rod, at least one rigid correction rod of circular cross section and at least one connector comprising a hook having a first semicylindrical seat oriented substantially along a first axis to receive said correction rod in a sliding manner, in which the transverse rod has at least one substantially spherical end and in which the connector has a second seat with an axis substantially perpendicular to the first axis, the second seat opening into the first seat and receiving the substantially spherical end of the transverse rod, said second seat comprising a tapped hole with an axis oriented substantially perpendicular to the axis of the second seat to receive a clamping screw which will exert a pressure on the spherical end of the transverse rod, said spherical end coming to bear on the correction rod.

The invention also concerns a transverse rod for an osteosynthesis system having at least one substantially spherical end, or even two substantially spherical ends, that is to say having the general shape of a dumbbell.

The diameter of the transverse rod at the level of the contact with the spherical end is less than the diameter of the spherical end, in order to ensure the necessary degree of freedom by rotation of the spherical end in the second seat.

It is conceivable to design the transverse rod in the general shape of a half-dumbbell, that is to say having only one substantially spherical end, for a connection at the substantially spherical end to the system described, and a connection on the other end of the transverse rod via another more conventional hook system. This alternative has the advantage of giving the connection the degree of freedom corresponding to the system described and of additionally offering the possibility of regulating the distance between the axes of the correction rods. In this alternative, all of the degrees of freedom for fitting the system are proposed.

The invention also concerns a method of implanting an osteosynthesis system comprising at least one transverse connection element which has a transverse rod, at least one rigid correction rod of circular cross section and at least one connector comprising a hook intended to be positioned on the correction rod, said connector having a first semicylindrical seat oriented substantially along a first axis and adapted to receive said correction rod in a sliding manner, and a second seat having an axis substantially perpendicular to the first axis, the second seat opening into the first seat and having a tapped hole with an axis oriented substantially perpendicular to the axis of the second seat in order to receive a clamping screw, the transverse rod having at least one substantially spherical end. According to this method, the substantially spherical end of the transverse rod of the transverse connection element is introduced into said second seat and the clamping screw will exert a pressure on the spherical end of the transverse rod, said spherical end bearing on the correction rod.

In a variant of this method, the clamping screw is introduced into the tapped hole before the positioning of the connector on the correction rod and after the introduction of the spherical end into the second seat, and in which the clamping screw is screwed only after the positioning of the connector on the correction rod; this spherical end then exerting a pressure on the correction rod.

According to this method, use is preferably made of a forceps with which it is possible to hold the connector on the correction rod as long as the clamping screw does not exert a pressure on the spherical end of the transverse rod.

BRIEF DESCRIPTION OF THE DRAWINGS

The invention will be better understood on reading the following description in which reference is made to the attached drawings, where:

FIGS. 8 and 9 show two perspective views of the use of the forceps with which it is possible to hold the hook on the correction rod as long as the clamping screw is not completely screwed in.

DETAILED DESCRIPTION OF THE PREFERRED EMBODIMENTS

The transverse connection element (1) has a general dumbbell or half-dumbbell shape. It is intended to link the longitudinal connection elements formed by rods. It has a median cylindrical segment forming a transverse rod (2) continued at one end or at each end (3) by a hemispherical part.

The transverse rod (2) can be rectilinear or, by contrast, arched in order to permit easier adaptation to the anatomy of the patient, for example in an omega shape. It has a circular or any other cross section.

Such an omega shape makes it possible to pass over the spinous processes of the vertebra which is being operated on. The distance between the axes of the two spherical ends (3), and hence the length of the rectilinear or arched transverse rod (2), differs depending on the spacing between the connection elements formed by rods or plates. In a complete system, a variety of connection elements with different spacings will advantageously be made available.

Figure 4:
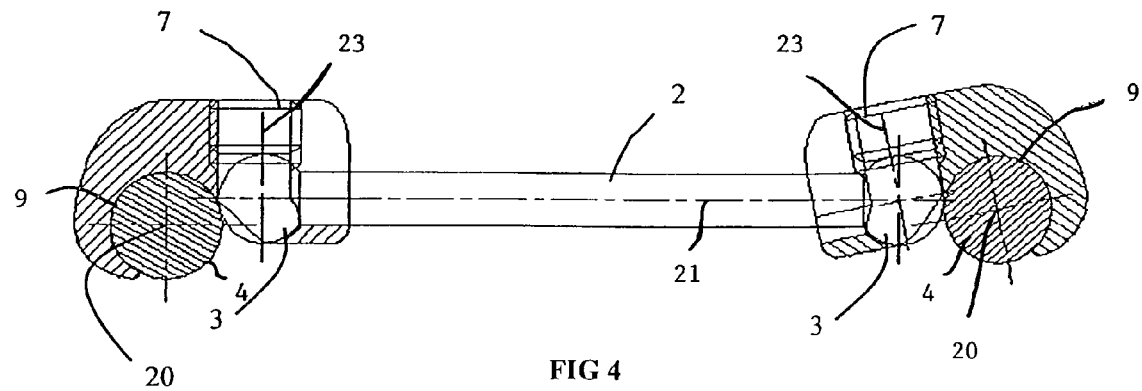
FIGS. 4 and 5 show two views of a system according to the invention.
Figure 5:
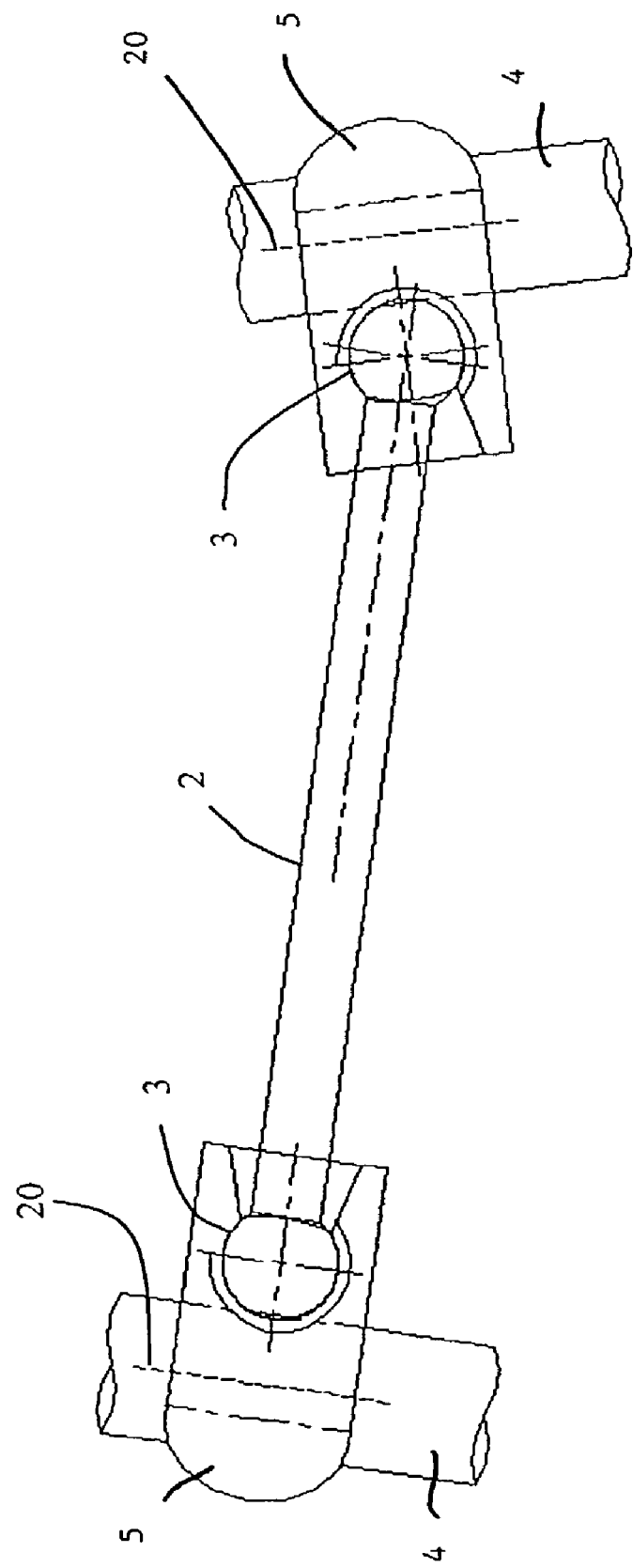

The spherical ends (3) of the transverse connection element come into contact with longitudinal connection elements, ensuring the correction of the spine and its realignment, as is represented in FIGS. 4 and 5.

Figure 1:
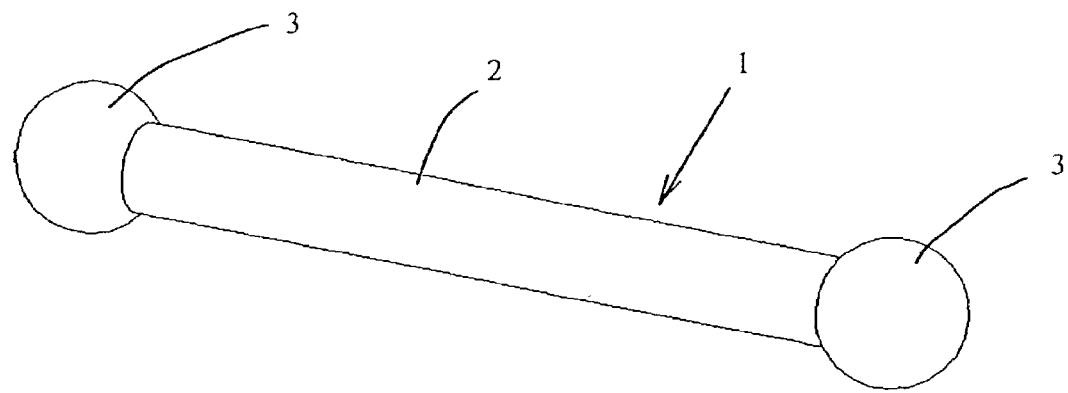
FIG. 1 shows a view of the transverse connection rod.
Figure 2:
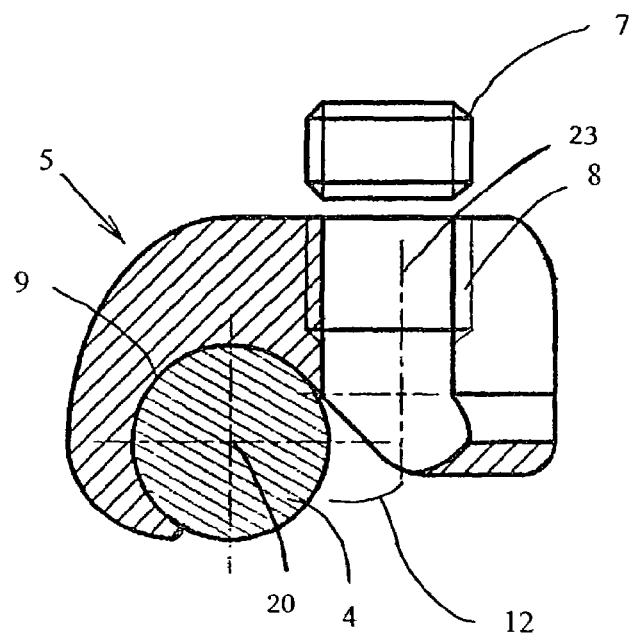
FIG. 2 shows a sectional view of the connection component.
Figure 3:
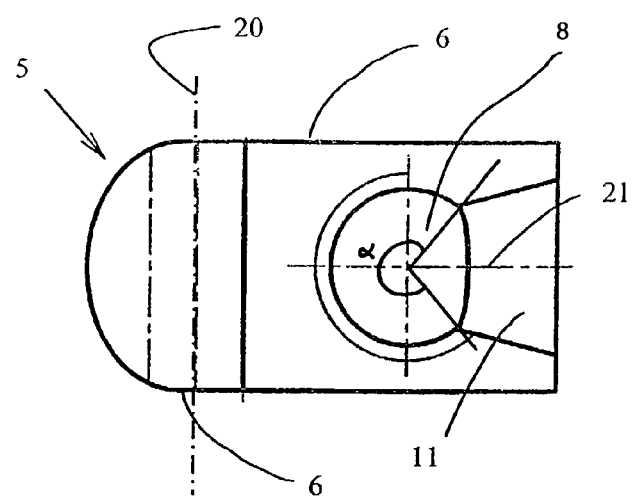
FIG. 3 shows a plan view of said connection component.

The connector (5) is formed by a nut shown in FIG. 2. It has a first semicylindrical seat (9) oriented substantially along a first axis (20), in order to receive a correction rod (4) of circular cross section. The connector (5) has a second seat (11) with an axis (21) substantially perpendicular to the first axis (20), this seat (11) opening into the first seat (9) and being intended to receive a substantially spherical end (3) of the transverse rod (2) of the transverse connection element (1).

The second seat (11) has a tapped hole (8) intended to receive a clamping screw (7) in such a way as to rigidly secure the whole system. The tapped hole (8) has an axis (23) oriented substantially perpendicular to the axis (21) of the second seat (11).

This same connector can also receive on its facets, for example on the lateral face (6), grip holes in order to facilitate the manipulation of the connector, or even the whole of the transverse connection system. The first semicylindrical seat (9) forms a groove receiving the longitudinal connection element.

The correction rod (4) is preferably a posterior rod or circular connection rod, which permits rotation thereof about its axis. This correction rod (4) is joined to the spine by way of bone implants. These implants are formed by hooks, pedicle screws or plates for fixing to the sacrum.

The connector (5) exerts a load on the correction rod (4) in a direction posterior to the patient, which represents in this case the transverse connection element. The connector (5) has a tapped hole (8) off-centered in relation to the axis (20) of the rod (4). This tapped hole (8) has a first function which is to receive the clamping screw (7) which locks the system.

It also has a second function which is to leave the passage free for the introduction of the spherical end (3) of the transverse component. For this purpose, the cross section of the bore of the tapped hole (8) is at least equal to the cross section of the spherical end (3) and merges into the opening of the second conical seat (11) intended for the passage of the transverse rod (2) of the transverse component.

Thus, the second seat (11) has a substantially semicylindrical shape along the axis (23) of the tapped hole (8).

The semicylindrical shape of the second seat preferably extends transversely at an angle of more than 180° and approximately 240°, in such a way as to promote the stability of the transverse rod in translation along its axis.

When all the constituent parts of the system are in position, the clamping screws (7) are introduced into the tapped holes (8) of the connectors (5).

The tightening of the clamping screw (7) means that the end of the screw (7) bears on the spherical end (3) of the transverse component, this spherical end (3) coming to bear on the correction rod (4). It thus ensures that the rod (4) is locked in its semicylindrical seat. The tightening of the screw (7) thus ensures simultaneous locking of all the components passing through the connector.

The conical shape of the second seat (11) permits a clearance of the transverse component, as is represented in FIGS. 4 and 5.

Such a system can be fitted in place in different ways:
  Positioning of a hook without its clamping screw on each of the correction rods (4), then insertion of the transverse rod (2) of general dumbbell shape and with a length adapted to the distance between the axes of said rods through the second seat (11) of each connector, then insertion and tightening of the clamping screws (7) on the connector in the tapped hole (8) provided for this purpose, for rigid connection of the assembly on the rods.
  Positioning of the pre-fitted system, the clamping screws (7) each just being introduced into the tapped holes (8) provided for this purpose, but not tightened, in such a way as to leave possible the introduction of the correction rods (4) into the first seats (9) of the hooks.

Figure 6:
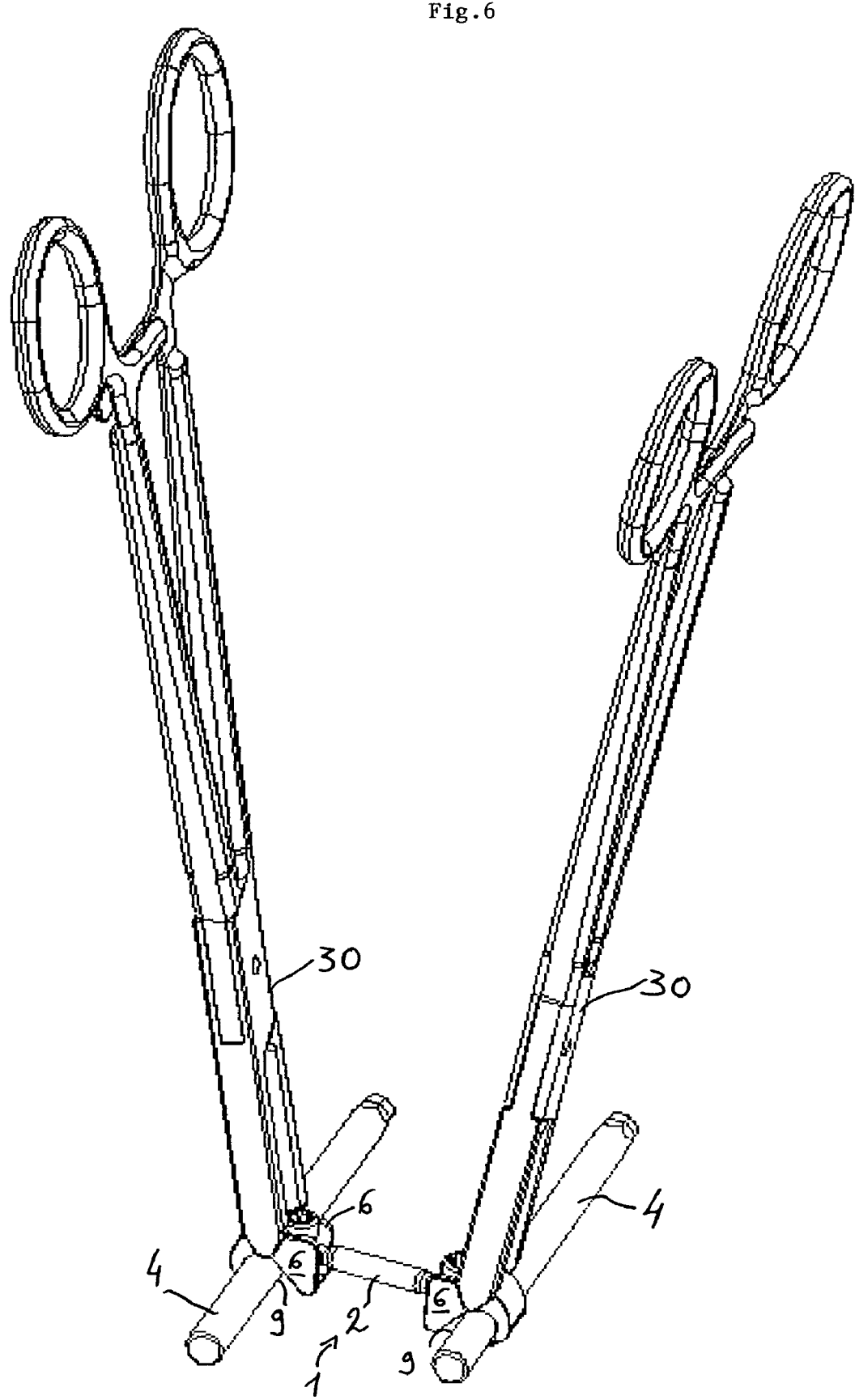
FIG. 6 shows a perspective view of an osteosynthesis system according to the invention fitted in a preliminary manner and held with the aid of a gripping forceps.
Figure 7:
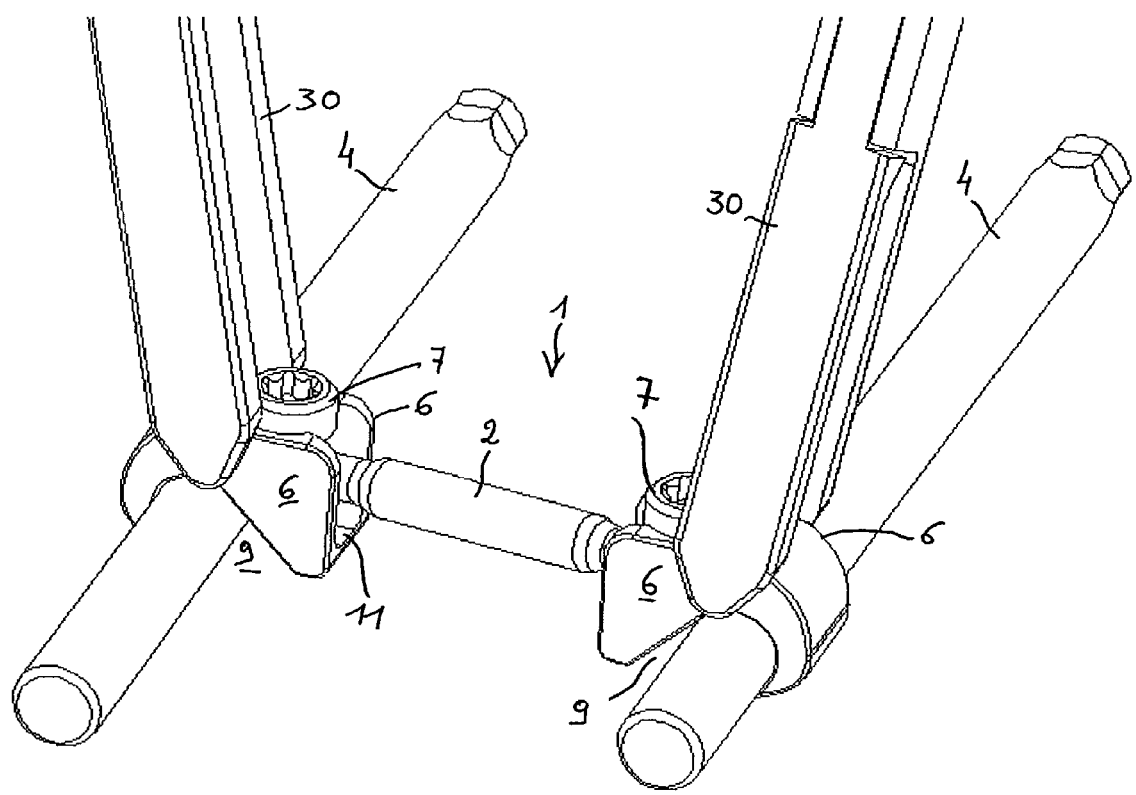
FIG. 7 shows a detail from FIG. 6.
Figure 8:
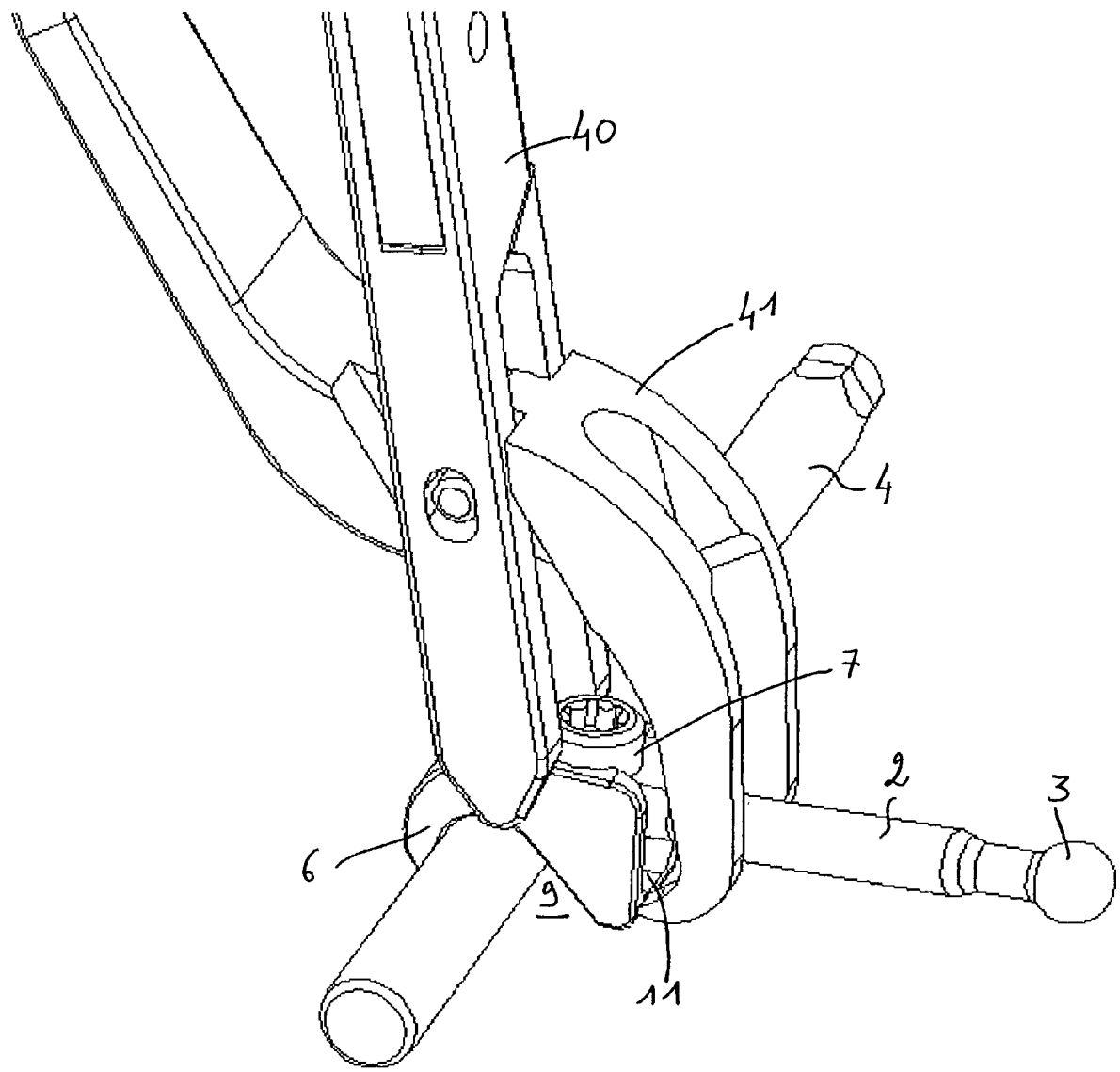

Various instruments are used for fitting the system in place:
  A gripping forceps (30) of the scissor type, as is illustrated in FIGS. 6 and 7. This forceps allows access for the passage of the correction rod, and also access to the tapped hole for introduction and tightening of the clamping screw (7). This gripping forceps (30) bears directly on the lateral faces (6) of the connector (5) or uses grip holes formed for this purpose on these faces.
  A distraction or compression forceps for defining the distance between the axes of the correction rods (4) (not shown).
  A forceps (40) with which it is possible to hold the hook on the correction rod (4) without tightening the clamping screw (7), as is illustrated in FIG. 8 in the open position and in FIG. 9 in the closed position. This forceps (40) bears directly on the lateral faces (6) of the connector (5) or uses grip holes formed for this purpose on these faces. It comprises a rod with rabbet (41) which is curved (31) and articulated relative to the forceps in order to permit the correction rod (4) to be maintained in the closed position.

What is claimed is:

1. A connector for an osteosynthesis system intended to provide a connection between a rigid correction rod of circular cross section and a transverse connection element of a spinal osteosynthesis system, said connector comprising:
  a hook having a first semicylindrical seat oriented substantially along a first axis, said hook receiving a correction rod in a sliding manner along the first axis;
  a second seat having a second axis substantially perpendicular to the first axis, said second seat opening into the first seat and receiving a substantially spherical end of a transverse rod of the transverse connection element along the second axis; and
  said second seat comprising a tapped hole with an axis oriented substantially perpendicular to the second axis of the second seat to receive a clamping screw which exerts a pressure on the spherical end of the transverse rod, said spherical end bearing on the correction rod.

2. The connector as claimed in claim 1, in which the second seat opens out via a widened conical portion to permit a cone of mobility of the transverse rod before the clamping screw is tightened.

3. The connector as claimed in claim 1, in which the second seat has a substantially semicylindrical shape along the axis of the tapped hole.

4. The connector as claimed in claim 1, in which the first semicylindrical seat extends about 180°.

5. The connector as claimed in claim 1, in which the tapped hole for receiving the clamping screw has a bore with a cross section at least equal to a cross section of the spherical end of the transverse connection element to permit passage of said spherical end through the tapped hole.

6. An osteosynthesis system comprising at least one transverse connection element which has a transverse rod, at least one rigid correction rod of circular cross section and at least one connector comprising a hook having a first semicylindrical seat oriented substantially along a first axis to receive said at least one rigid correction rod in a sliding manner along the first axis, the transverse rod having at least one substantially spherical end, and the connector having a second seat with a second axis substantially perpendicular to the first axis, said second seat opening into the first seat and receiving the at least one substantially spherical end of the transverse rod of the transverse connection element along the second axis, said second seat comprising a tapped hole with an axis oriented substantially perpendicular to the second axis of the second seat to receive a clamping screw which exerts a pressure on the at least one spherical end of the transverse rod, said at least one spherical end bearing on the correction rod.

7. A method of implanting an osteosynthesis system comprising at least one transverse connection element which has a transverse rod, at least one rigid correction rod of circular cross section and at least one connector comprising a hook to be positioned on the correction rod, said at least one connector having a first semicylindrical seat oriented substantially along a first axis and to receive said at least one correction rod in a sliding manner along the first axis, and a second seat having a second axis substantially perpendicular to the first axis, said second seat opening into the first seat and having a tapped hole with an axis oriented substantially perpendicular to the second axis of the second seat to receive a clamping screw, the transverse rod having at least one substantially spherical end, said method comprising:

introducing the substantially spherical end of the transverse rod of the at least one transverse connection element into said second seat along the second axis; and exerting a pressure on the substantially spherical end of the transverse rod with a clamping screw so that said substantially spherical end bears on the correction rod.

8. The method of implanting an osteosynthesis system as claimed in claim 7, further comprising introducing the clamping screw into the tapped hole before the positioning of the connector on the correction rod and after the introduction of the substantially spherical end into the second seat, and screwing the clamping screw only after the positioning of the connector on the correction rod.

9. The method of implanting an osteosynthesis system as claimed in claim 7, further comprising holding the connector on the correction rod using a forceps as long as the clamping screw does not exert a pressure on the substantially spherical end of the transverse rod.

* * * * *